United States Patent [19]
Smits

[11] Patent Number: 5,397,343
[45] Date of Patent: Mar. 14, 1995

[54] MEDICAL ELECTRICAL LEAD HAVING COUNTER FIXATION ANCHORING SYSTEM

[75] Inventor: Karel F. A. A. Smits, Oirsbeck, Netherlands

[73] Assignee: Medtronic, Inc., Minneapolis, Minn.

[21] Appl. No.: 164,235

[22] Filed: Dec. 9, 1993

[51] Int. Cl.⁶ ............................................. A61N 1/05
[52] U.S. Cl. ..................................... 607/130; 607/120
[58] Field of Search ............... 607/130, 129, 119, 120; 128/642

[56] References Cited

U.S. PATENT DOCUMENTS

| | | | |
|---|---|---|---|
| 4,010,758 | 3/1977 | Rockland et al. | 128/418 |
| 4,144,890 | 3/1979 | Hess | 128/418 |
| 4,149,542 | 4/1979 | Thorén | 128/418 |
| 4,177,818 | 12/1979 | De Pedro | 128/418 |
| 4,258,725 | 3/1981 | O'Neill | 128/419 P |
| 4,313,448 | 2/1982 | Stokes | 607/130 |
| 4,469,104 | 9/1984 | Peers-Trevarton | 128/419 P |
| 4,506,680 | 3/1985 | Stokes | 128/786 |
| 4,572,605 | 2/1986 | Hess | 339/177 R |
| 4,577,642 | 3/1986 | Stokes | 128/784 |
| 4,603,704 | 8/1986 | Mund et al. | 128/784 |
| 4,606,118 | 8/1986 | Cannon et al. | 29/825 |
| 4,677,989 | 7/1987 | Robblee | 128/784 |
| 4,711,251 | 12/1987 | Stokes | 128/784 |
| 4,773,433 | 9/1988 | Richter et al. | 128/784 |
| 4,784,160 | 11/1988 | Szilagyi | 128/784 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,898,173 | 2/1990 | Daglow et al. | 128/419 P |
| 4,972,848 | 11/1990 | Di Domenico et al. | 128/785 |
| 5,007,435 | 4/1991 | Doan et al. | 128/784 |
| 5,070,605 | 12/1991 | Daglow et al. | 29/842 |
| 5,085,218 | 2/1992 | Heil, Jr. et al. | 128/642 |
| 5,143,090 | 9/1992 | Dutcher et al. | 128/785 |
| 5,154,183 | 10/1992 | Kreyenhagen et al. | 128/785 |

FOREIGN PATENT DOCUMENTS 0087130  8/1983  European Pat. Off. .............. 607/130

*Primary Examiner*—William E. Kamm
*Assistant Examiner*—Kennedy J. Schaetzle
*Attorney, Agent, or Firm*—Michael J. Jaro; Harold R. Patton

[57] ABSTRACT

An epicardial lead having an stab-in electrode extending from the bottom thereof in combination with an anchoring system adapted to secure the lead to the heart without the use of complex procedures or tools. In particular the lead achieves stable fixation through the provision of a flexible member moveable between a first position and a second position and a pair of fixation members connected to said flexible member, each fixation member having a distal end and a root, said distal end and root defining a plane said through which said stab-in electrode crosses.

18 Claims, 4 Drawing Sheets

MEDICAL ELECTRICAL LEAD HAVING COUNTER FIXATION ANCHORING SYSTEM

BACKGROUND OF THE INVENTION

1. Field of the Invention

This invention relates to medical leads for providing electrical signals to a heart, and more particularly, to an epicardial lead having an anchoring system providing stable fixation to the heart and adapted for simple and quick attachment.

2. Description of the Prior Art

Heart leads are used to provide an electrical connection between a pulse generator and a patient's heart. In a great majority of the cases where the pulse generator is implanted within a patient on a permanent basis, transvenous leads are used, wherein the lead is introduced into the heart through a convenient vein. This procedure avoids the requirement of having to establish direct access to the heart itself. Such leads also avoid the trauma of actually inserting the lead into the heart wall. The endocardial lead as disclosed in U.S. Pat. No. 4,506,680 to Stokes, for example, has proven very successful for use in a large majority of cases.

In a certain percentage of cases, however, it is deemed necessary or desirable to use an external or epicardial lead, wherein the electrode or electrodes are mechanically inserted into the epicardium. In this arrangement, it is necessary the insertion be made with a minimum of trauma but yet be absolutely secure so that good electrical contact is maintained with the heart. Historically, one form of such epicardial lead has involved actually suturing the lead onto the heart wall to thereby insure the required security. This has the great disadvantage, however, of increasing the complexity of the operative procedure required to implant such a lead.

To overcome the difficulties and complexities presented by use of a sutured epicardial lead, the medical device industry has developed a screw-in epicardial lead. This lead consists of a helical coil which is screwed into the heart wall. Examples of such a lead are disclosed in U.S. Pat. No. 5,154,183 to Kreyenhagen et al., U.S. Pat. No. 5,143,090 to Dutcher et al., U.S. Pat. No. 5,085,218 to Heil Jr. et al. and U.S. Pat. No. 4,010,758 to Rockland et al. This type of lead, however, requires sufficient room to approach the heart wall from a direction more or less perpendicular to the surface to enable the helical coil to be screwed directly into the heart muscle. Even if a perpendicular approach is not required, the physician must still have sufficient access to the heart so as to be able to push the helical coil tip into the epicardium and rotate it.

An alternative to a screw-in lead may be seen in U.S. Pat. No. 4,177,818 to DePedro which discloses an epicardial electrode constructed from a pliable material and having a series of fixation prongs. This lead, however, requires the use of a tool or instrument to deform the lead body back against itself in order to attach it to the heart surface. A variation on such a flexible epicardial lead is disclosed in U.S. Pat. No. 4,144,890 to Hess which shows a lead which must be flexed forward with a tool, rather than backward, against itself in order to insert it into the epicardium.

While these leads have enjoyed a reasonable success to date, there remains a need for a simpler type of epicardial lead which reduces the procedures and tools required of the physician to secure the lead to the heart. In addition, it is also important that such a lead still provide, because the heart is an organ constantly undergoing contractile movements, a stable anchor of the lead to the heart.

SUMMARY OF THE INVENTION

It is an object of the invention to provide an epicardial lead which permits the securing of such lead to the epicardium of a patient's heart or to another organ of the patient, which lead is simple to use, provides a highly stable fixation, and does not require an elaborate engaging tool.

It is a further object of the invention to provide an epicardial lead which permits the delivery of a drug in the region proximate the electrode-tissue interface.

In accordance with the above objects there is provided an epicardial lead having a drug eluting stab-in electrode extending from the bottom thereof in combination with a pair of fixation members. Each fixation member is mounted to a flexible member. The fixation members are, moreover, positioned in a counter direction from the stab-in electrode and are, in fact positioned such that the plane defined by the fixation members is crossed by the stab-in electrode. In such a manner the fixation members and stab-in electrode cooperate so that the contractile movement of the heart tends to increase the anchoring of the lead to the heart. The fixation members, moreover, are designed so that the electrode may be first brought into contact with the heart tissue before the lead is fixed to the heart. Through such a design the optimal electrode position may be determined before the trauma of lead fixation is initiated. In such a fashion an epicardial lead is provided which permits implantation without any tools and also provides stable anchoring to the heart.

DESCRIPTION OF THE PREFERRED EMBODIMENTS

Figure 1:
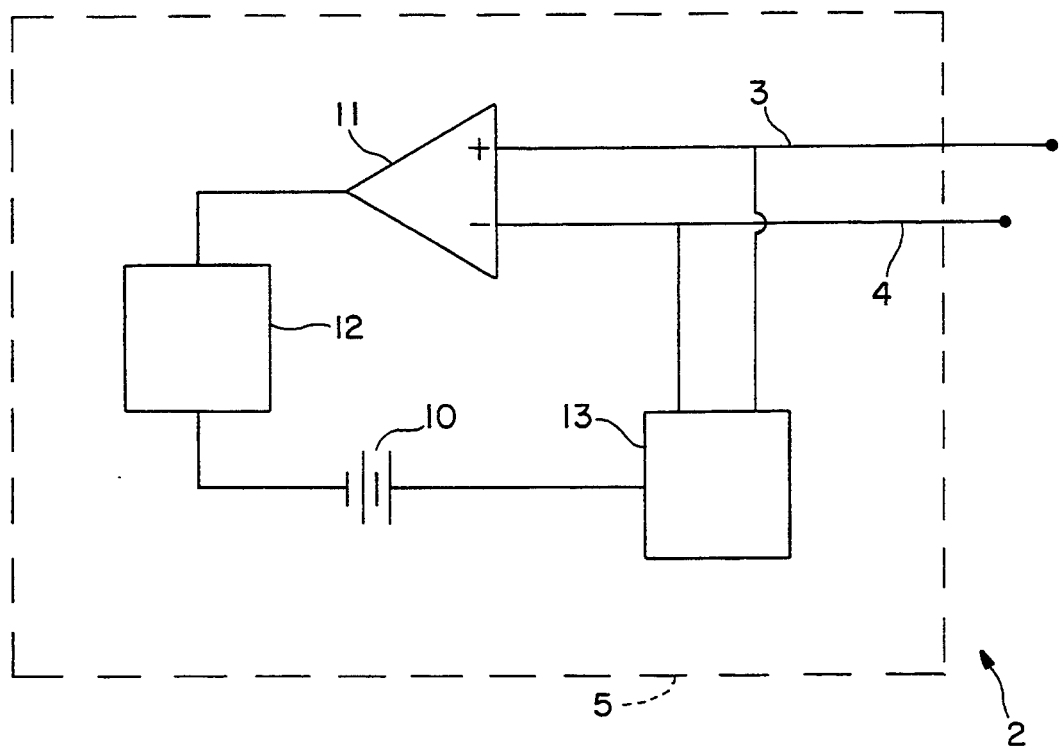
FIG. 1 is a schematic view of a lead in use with an implantable pulse generator system.

FIG. 1 is a schematic view of a lead in use with a pacing system 2, showing conductors 3, 4 electrically connected to an implantable pulse generator 5. Implantable pulse generator 5 is constructed from a battery 10, a sense amp 11, a microprocessor 12, and an output amp 13. Through such a pacing system 2 the lead of the present invention may be used to electrically stimulate and sense body tissue, such as a heart.

Figure 2:
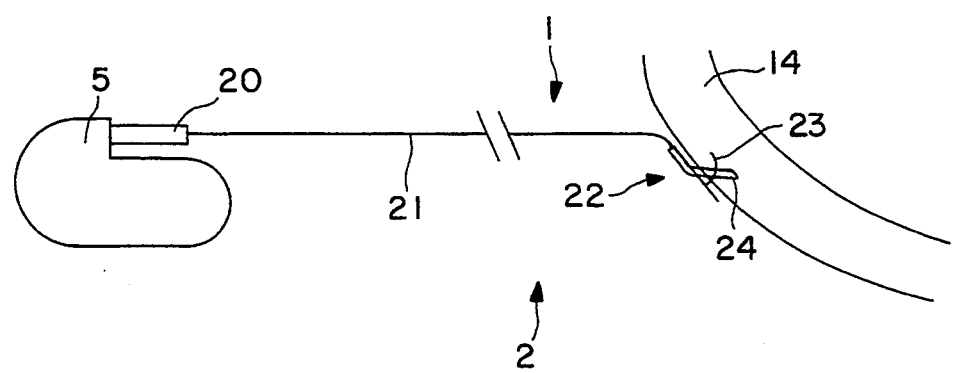
FIG. 2 is a lead according to the present invention in use with an implantable pulse generator system.

FIG. 2 shows a lead 3 according to the present invention in use as part of a pacing system 2 and implanted within a heart 14. Lead 1, as seen, has essentially five parts or sections: connector 20, lead body 21, lead head 22, fixation members 23 and stab-in electrode 24.

Figure 3:
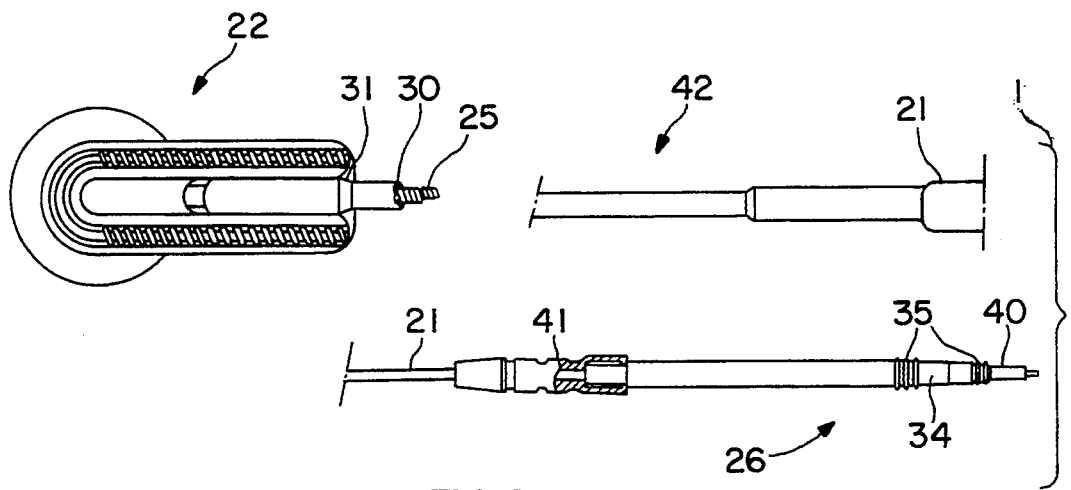
FIG. 3 is a plan view of a lead constructed in according to the present invention.
Figure 4:
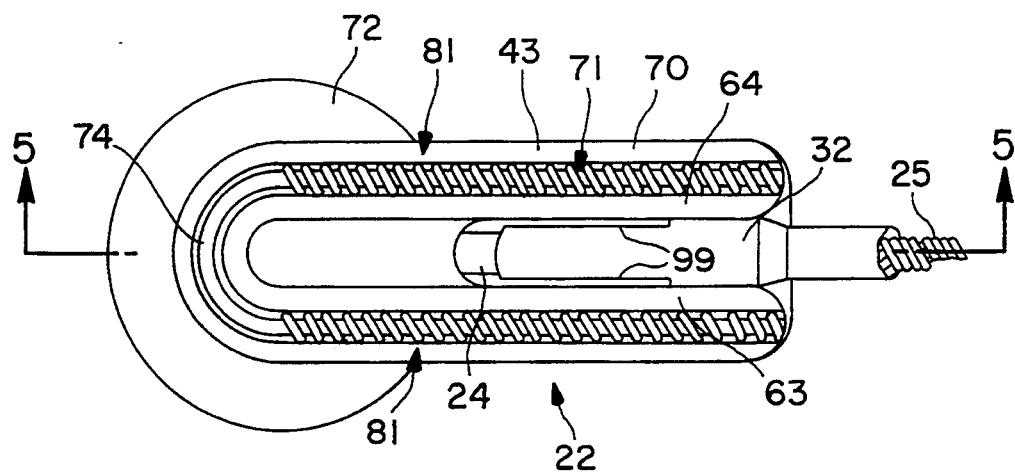
FIG. 4 is a plan view of the top side of a lead head according to the present invention.
Figure 6:
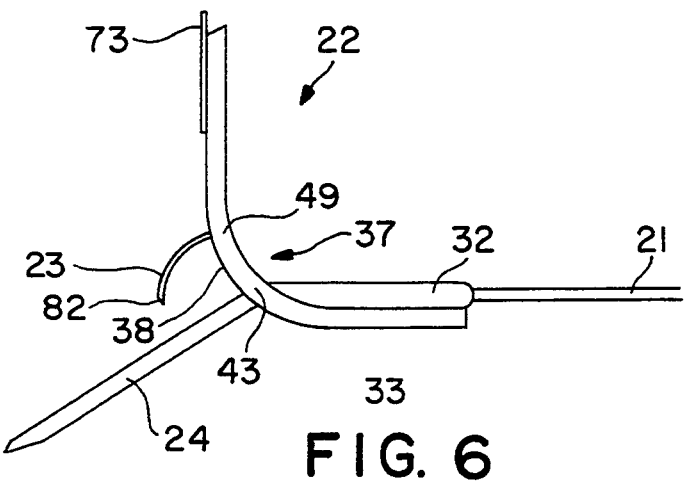
FIG. 6 is a side view of the lead head having the flexible member retracted so the lead head may be attached to the heart.
Figure 7:
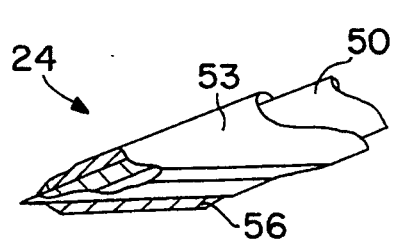
FIGS. 7–14 each show a detail of an alternative design for a stab-in electrode.

Referring to FIG. 3, a lead 4 constructed according to the present invention is shown. As seen, lead 1 comprises elongated lead body 21 and lead head 22. Lead body 21 comprises a standard arrangement of a coiled conductor 25 or conductors (partially shown in cutaway) encased in a suitable insulating cover 30 of a biocompatible material, such as silicone or a urethane material. At distal end 31 of elongated lead body 21, as shown, lead head 22 is located. As seen in FIG. 4 lead head 22 is constructed from electrode mounting 32 and flexible member 43. Electrode mounting 32 has stab-in electrode 24 extending from its bottom surface 33. Flexible member 43 has a pair of fixation members 23 extending from bottom surface 38 as best seen in FIG. 6 (only a single fixation member 23 may be seen, however, due to the plan view.) Fixation member 23 are positioned so that they define a plane shown as dotted line 48 between their root region 49 and tip portion 82 through which stab-in electrode 24 crosses.

Although FIG. 3 illustrates a plan view of lead 1 constructed in accordance with the present invention. It should be noted, however, the relative proportions of lead 1, and especially lead head 22 are not shown to scale.

Lead 1 includes an elongated lead body 21 comprising a length of coiled conductor 25 and an insulative cover 30 as is well known in the art. Insulative cover 30 may be fabricated of any flexible biocompatible and biostable insulator especially silicone rubber or polyurethane.

At proximal end 26 of elongated lead body 21, terminal assembly 34 is adapted to couple lead 1 to a pulse generator 5. Terminal assembly 34 is provided with sealing rings 35 and a terminal pin 40, all of a type known in the art.

An anchoring sleeve 41 (shown partially in cross-section) slides over insulative cover 30 and serves as a point for suturing elongated lead body 21 to body tissue in a fashion known in the art. Anchoring sleeve 41 and terminal assembly 34 are preferably fabricated of silicone rubber, although they may also be constructed of any other suitable biocompatible material known in the art.

Lead body 21 features reduced diameter portion 42 to provide greater flexibility proximate lead head 22 as is well known in the art. The specific design and construction of elongated lead body 21 and terminal assembly 34 are not within the scope of the present invention. Further detail and description of the construction of an elongated lead body 21 and terminal assembly 34 suitable for use with the present invention may be seen, for example, in Daglow et al. U.S. Pat. Nos. 5,070,605 and 4,898,173; Doan et al., U.S. Pat. No. 5,007,435; Hess, U.S. Pat. No. 4,572,605; Peers-Trevarton, U.S. Pat. No. 4,469,104; and O'Neil, U.S. Pat. No. 4,258,725, all incorporated herein by reference.

Figure 5:
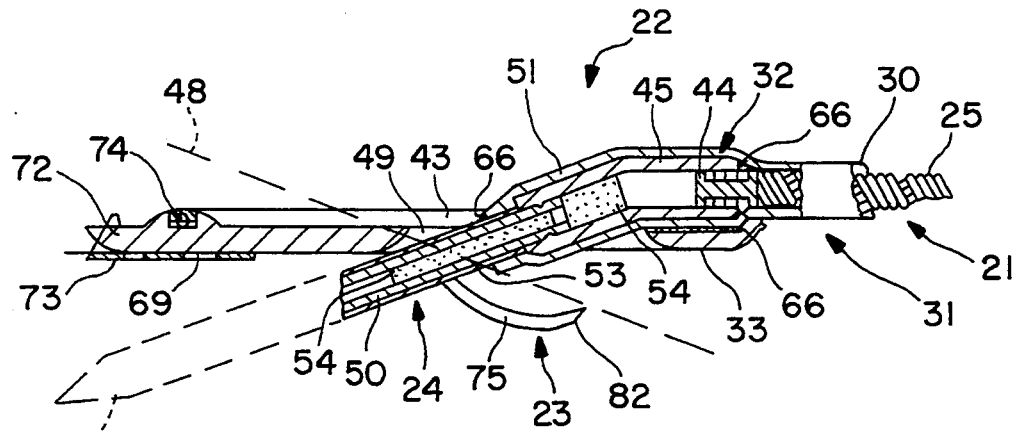
FIG. 5 is a cross-sectional view of a lead head according to the present invention.

As best seen in FIGS. 5 and 6 lead head 22 is fixed to distal end 31 of elongated lead body 21. Lead head 22 comprises electrode mounting 32 and flexible member 43. In the preferred embodiment, electrode mounting 32 is affixed to distal end 31 of elongated lead body 21 by adhesive generally indicated as 66 throughout. Suitable adhesives include a silicone medical adhesive as is well known in the art. Electrode mounting 32 is constructed from polyurethane, although other biocompatible materials may also be used such as silicone.

Mounted along bottom surface 33 of electrode mounting 32, as seen in FIG. 5, is stab-in electrode 24 (shown partially in phantom for clarity.) Stab-in electrode 24 is preferably constructed from a platinum-iridium alloy. Stab-in electrode 24 may further be constructed from a porous platinum covered with platinum black. Although platinum is the preferred material for stab-in electrode 24, it may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others, such as a platinum with a titanium, and may not be effectively used together. The limitations of specific materials for use with others is well known in the art.

Stab-in electrode 24 is suitably connected to coiled conductor 25 of elongated lead body 21 to provide the necessary mechanical and electrical contact between stab-in electrode 24 and terminal assembly 34. As seen in FIG. 5 stab-in electrode 24 is connected to coiled conductor 25 by crimp core 44 and crimp tube 45. Crimp tube 45 is crimped about coiled conductor 25. Crimp tube 45 is further crimped to hollow electrode member 50. Surrounding hollow electrode member 50 and coiled conductor 25 is skirt 51. Further hollow electrode member 50 is insulation 53. Insulation 53 may be constructed from silicone. As seen two cores 54 are positioned within stab-in electrode 24.

Each core 54 functions as a monolithic controlled release device and may be constructed from polyurethane or any other appropriate polymer. Through such materials core 54 may preferably be loaded with an anti-inflammatory drug, e.g., asteroid such as dexamethasone sodium phosphate, which will elute from core 54 through stab-in electrode 24 and into surrounding body tissue to reduce inflammatory response and tissue ingrowth. Further description of the construction, use and advantages of a monolithic controlled release device incorporating steroid with an implantable lead may be seen, for example in Stokes, U.S. Pat. No. 4,506,680 and related Medtronic U.S. Pat. Nos. 4,577,642; 4,606,118; 4,711,251 and 4,972,848 all incorporated herein by reference.

Stab-in electrode 24 is preferably configured to allow the steroid or other anti-inflammatory agent to be eluted through and/or around in order to reach the endocardial or myocardial cells proximate thereto and reduce the acute and chronic inflammation occasioned by the cellular foreign body and physical irritation response to the lead head 22. As described in Stokes, U.S. Pat. No. 4,506,680 and related Medtronic U.S. Pat. Nos. 4,577,642; 4,606,118 and 4,711,251, mentioned above, asteroid eluting electrode is fabricated from a body compatible electrically conductive material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a microscopic (or "fractal") large surface area for sensing and a macroscopic or geometrically measured very small surface area for stimulation. Acceptable electrode materials and the associated fabrication techniques employed to achieve the microporous structure, as well as the porosity of that structure are all set forth in the aforementioned prior art patents and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161 and Szilagyi, U.S. Pat. No. 4,784,160, herein incorporated by reference and other patents and literature in the prior art.

Figure 8:
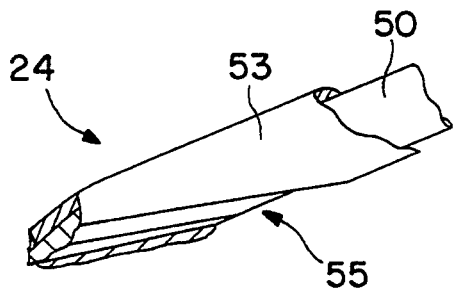
Figure 9:
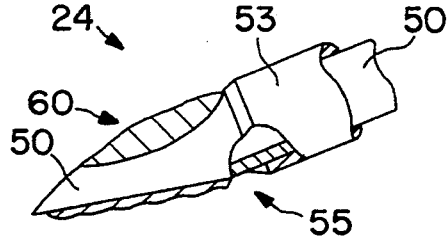
Figure 10:
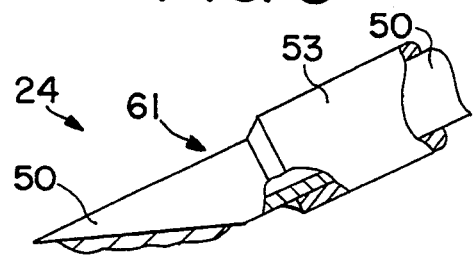
Figure 11:
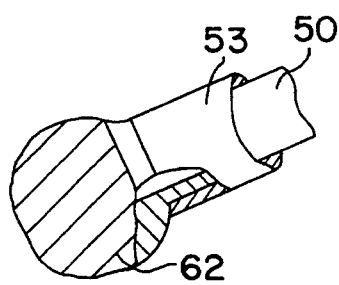
Figure 12:
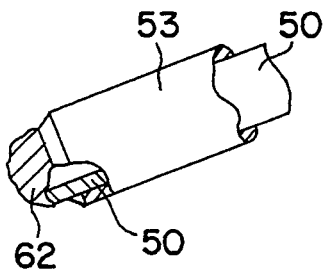
Figure 13:
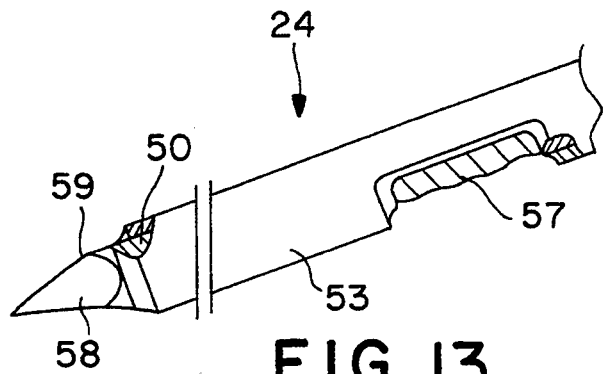
Figure 14:
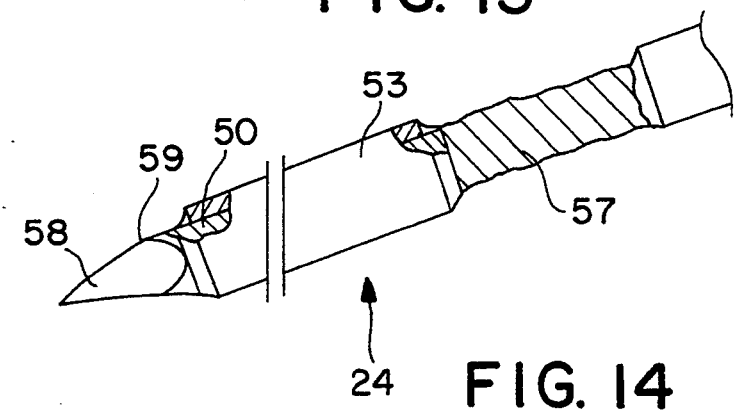

Further embodiments of stab-in electrode 24 for use in a lead constructed according to the present invention are shown in FIGS. 7–14. Stab-in electrode 24 of FIG. 2 is constructed from hollow electrode member 50, insulation 53, and porous tip 56. Porous tip 56 is preferably constructed from a porous platinum powder as is well know in the art. Stab-in electrode 24 of FIG. 8 is substantially similar to that of FIG. 7 but for bevel tip portion 55. Stab-in electrode 24 of FIG. 9 is a variant of stab-in electrode 24 of FIG. 8 and features a bevelled tip portion 55 with porous window 60 and has exposed hollow electrode member 50. Stab-in electrode 24 of FIG. 10 is substantially similar to that seen in FIG. 9 but for the exposed distal end 61 of hollow electrode member 50. FIGS. 11 and 12 depict further alternate stab-in electrodes 24 having a ball-shaped porous tip 62. FIGS. 13 and 14 depict further alternate embodiments of a stab-in electrode 24 suitable for use in the present invention. As seen each of these embodiments is constructed similar to those above, i.e. from hollow electrode member 50 partially covered by insulation 53 except featuring a porous electrode portion 57 set away from the tip region 58. The exact location of porous electrode portion 57 along hollow electrode member 24 may be fashioned as desired, as seen these include both a fully cylindrical section, FIG. 14, and a partially cylindrical section, FIG. 13. Set within hollow electrode member 50 is plug portion 59 having a pointed tip. The advantage offered by the electrode configurations shown in FIGS. 13 and 14 is that less mechanical loading is experienced in the electrically active region of the electrode. As such, less tissue inflammation is experienced at that location and better performance will result.

Attached at opposing sides 63, 64 of electrode mounting 32 is flexible member 43. As seen, flexible member 43 attaches to opposing sides 63, 64 about opening 99. Flexible member 43 is a composite structure comprising flexible beam 70 and pad spring 71. Flexible beam 70 is molded, like electrode mounting 32, from polyurethane, although other biocompatible materials may also be used such as silicone. Pad spring 71 functions to provide a bias to flexible member 43 in the region of bend, shown generally as 37 in FIG. 6. In addition pad spring 71 further functions to maintain the bias of flexible beam 70 from cold flow. During chronic implantation the constant contractile motion of the heart may cause the polymer used to form flexible beam 70 to flow to the open position (as seen in FIG. 6.) Provision of pad spring 71 integral therewith maintains flexible beam 70 in the proper orientation, and thus fixation members 23 attached thereto. Flexible beam 70, in turn, also features pad 72 having along bottom surface 69 mesh material 73, preferably a DACRON polyester material or some other suitable body compatible material, to promote tissue ingrowth and thereby further lead implantation stability. Such ingrowth would function to further lock fixation member 23 and thus lead 1 in place.

Mounted to flexible member 43 is fixation member 23. Fixation member 23 is an integral piece having essentially two portions: mounting portion 74 and fixation portion 75. Mounting portion 74 is fitted to flexible member 43, and specifically within groove 80 in flexible beam 70. In region 81 mounting portion 74 runs through lumen of pad spring 71. Fixation portion 75, in the preferred embodiment, is essentially arcuate. To be precise, there are two fixation portions 75, one each extending from each side of flexible member 43 and having tip portion 82. Through such a configuration, fixation portion 75 follows a circular path as flexible member 43 is rotated between the positions depicted in FIG. and 5 to that shown FIG. 6, respectively, to thereby minimize tissue injury during implantation, although other shapes may also be used. In the preferred embodiment fixation member 23 is constructed from a platinum-iridium alloy.

Lead head 22 is attached to cardiac tissue (not shown) as follows. Flexible member 43 is moved from its biased position, as seen in FIG. 5 to the open position as shown in FIG. 6 respectively. Flexible member 43 is configured so it may be manipulated by hand and without requiring the use of special tools. Tips 82 (only one of which is seen in FIGS. 5 and 6 due to the plan view) of fixation member 23 are preferably sharpened. In the open position fixation member 23 is positioned above bottom surface 33 of electrode mounting 32, i.e. tips 82 of fixation member 23 are above bottom surface 33. Lead head 22 is next positioned so stab-in electrode 24 is inserted within heart tissue (not shown.) If acceptable results are not exhibited stab-in electrode 24 is withdrawn and reinserted. Once an acceptable site has been found flexible member 43 is lowered such that fixation members are inserted into the tissue. Through such a design the optimal stab-in electrode position may be determined before the trauma of lead fixation is initiated.

As seen, fixation member 23 and stab-in electrode 24 interact to provide a stable fixation of lead 1 to cardiac tissue (not shown). Specifically because fixation member 23 define a plane 48 through which stab-in electrode 24 crosses, contractile motion of the heart tends to further squeeze lead 1 against the heart, and in particular assists in maintaining contact with stab-in electrode 24.

Figure 15:
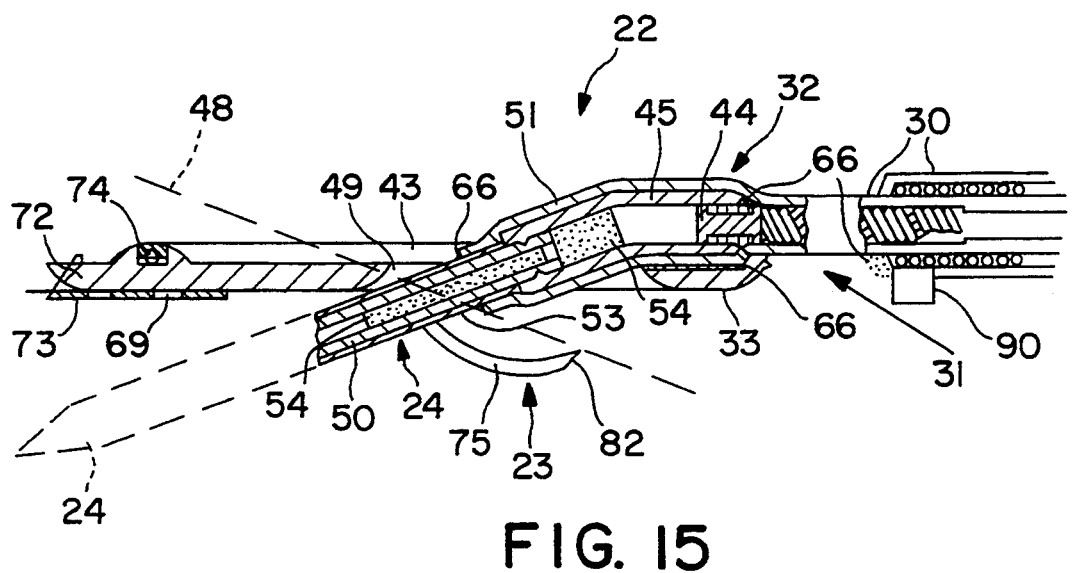
FIG. 15 is a side plan view of an alternative design for a lead head according to the present invention.

While lead 1 constructed according to the present invention has been described as a unipolar lead, it should be understood the present invention could also be incorporated as a bipolar, or even multipolar lead. Such a lead may be seen in FIG. 15 which shows a side plan view of a bipolar lead head according to the present invention. As seen a lead head similar to that previously described except with the addition of second electrode 90 provided on electrode mounting 32. Alternative designs for a bipolar configuration could also be accomplished by provision of a pair of stab-in electrodes 24. Alternatively one or both fixation members could be utilized to also provide electrical contact with the heart.

While the present invention have been described in particular application to an epicardial lead, it will also be understood the invention may be practiced in lead and other electrode technologies where the aforementioned characteristics are desirable, including muscle stimulation applications. Moreover, although the invention has been described in detail with particular reference to a preferred embodiments thereof, it will be understood variations and modifications can be effected within the scope of the following claims.

What is claimed is:

1. An epicardial lead adapted for attaching to a heart comprising:
   a lead body, said lead body having a conductor and an insulating sheath, said lead body having a distal end and a proximal end;
   a electrode mounting attached to said distal end of said lead body;
   a stab-in electrode attached at an angle to said mounting, said electrode having a distal end and a proximal end, said proximal end of said electrode connected to said conductor, said electrode configured to contact said heart; and
   a flexible member connected to said electrode mounting, said flexible member having a pair of fixation members thereto, each said fixation member having a distal end and a root, said distal end and root defining a plane through which said stab-in electrode crosses, said flexible member moveable between a first position and a second position wherein in said first position said distal ends of said fixation members are positioned below said stab-in electrode and in said second position said distal ends of said fixation members are positioned above said stab-in electrode.

2. A lead according to claim 1 wherein said fixation members are shaped to engage said heart and attach said lead thereto when said flexible member is moved from said second position to said first position.

3. A lead according to claim 2 wherein each said fixation member is arcuate.

4. A lead according to claim 1 further comprising means for delivering a drug to said heart.

5. A lead according to claim 1 wherein said flexible member has a spring integral therewith.

6. A lead according to claim 1 wherein said stab-in electrode has a hollow electrode member having a porous tip, said electrode member partially covered by an insulative material.

7. An epicardial lead adapted for attaching to a heart comprising:
   a lead body, said lead body having a conductor and an insulating sheath, said lead body having a distal end and a proximal end;
   a electrode mounting attached to said distal end of said lead body;
   a stab-in electrode attached at an angle to said mounting, said electrode having a distal end and a proximal end, said proximal end of said electrode connected to said conductor, said electrode configured to contact said heart;
   a flexible member connected to said electrode mounting, said flexible member moveable between a first position and a second position, said flexible member having a spring integral therewith, said flexible member biased towards said first position by said spring; and
   a pair of fixation members connected to said flexible member, each said fixation member having a distal end and a root, said distal end and root defining a plane said through which said stab-in electrode crosses.

8. A lead according to claim 7 wherein said fixation members are shaped to engage said heart and attach said lead thereto when said flexible member is moved from said second position to said first position.

9. A lead according to claim 8 wherein each said fixation member is arcuate.

10. A lead according to claim 7 further comprising means for delivering a drug to said heart.

11. A lead according to claim 7 wherein said stab-in electrode has a hollow electrode member having a porous tip, said electrode member partially covered by an insulative material, said electrode member having means for delivering a drug to said heart from said hollow electrode member.

12. An epicardial lead adapted for attaching to a heart comprising:
   a lead body, said lead body having a conductor and an insulating sheath, said lead body having a distal end and a proximal end;
   a electrode mounting attached to said distal end of said lead body;
   a stab-in electrode attached at an angle to said mounting, said electrode having a distal end and a proximal end, said proximal end of said electrode connected to said conductor, said electrode configured to contact said heart, said stab-in electrode having means for delivering a drug to said heart;
   a flexible member connected to said electrode mounting, said flexible member moveable between a first position and a second position, said flexible member biased towards said first position; and
   a pair of fixation members connected to said flexible member, each said fixation member having a distal end and a root, said distal end and root defining a plane said through which said stab-in electrode crosses.

13. A lead according to claim 12 further said fixation members are shaped to engage said heart and attach said lead thereto when said flexible member is move from said second position to said first position.

14. A lead according to claim 12 wherein each said fixation member is arcuate.

15. A lead according to claim 12 wherein said flexible member has a spring integral therewith.

16. A lead according to claim 12 wherein said stab-in electrode has a hollow electrode member having a porous section, said electrode member partially covered by an insulative material.

17. A lead according to claim 16 wherein said porous section is located at a tip of said hollow electrode member.

18. A lead according to claim 16 wherein said porous section is cylindrical.

* * * * *